United States Patent [19]

Briet et al.

[11] Patent Number: 4,783,533

[45] Date of Patent: * Nov. 8, 1988

[54] [OXO-4-4H-[1]-BENZOPYRAN-8-YL]AL-CANOIC ACIDS, SALTS AND DERIVATIVES, THEIR MANUFACTURE AND MEDICINES CONTAINING THEM

[75] Inventors: Philippe Briet, Lyons; Jean-Jacques Berthelon, Decines Charpieu; François Collonges, Beynost Miribel, all of France

[73] Assignee: Lipha, Lyonnaise Industrielle Pharmaceutique, Lyons, France

[*] Notice: The portion of the term of this patent subsequent to Jul. 22, 2003 has been disclaimed.

[21] Appl. No.: 872,381

[22] Filed: May 29, 1986

Related U.S. Application Data

[63] Continuation of Ser. No. 669,037, Nov. 6, 1984, Pat. No. 4,602,034, which is a continuation of Ser. No. 442,191, Nov. 15, 1982, abandoned.

Foreign Application Priority Data

Nov. 25, 1981 [FR] France .................. 81 22020

[51] Int. Cl.⁴ ................... A61K 31/35; C07D 311/26
[52] U.S. Cl. ................... 514/456; 549/403; 514/233.5
[58] Field of Search ............ 549/403, 401, 60; 544/146, 151; 514/230, 236, 444, 456

[56] References Cited

U.S. PATENT DOCUMENTS

| | | | |
|---|---|---|---|
| 2,921,070 | 1/1960 | Da Re | 549/403 |
| 3,770,802 | 11/1973 | Sianesi | 549/403 |
| 4,079,139 | 3/1978 | Gay | 549/403 |
| 4,097,582 | 6/1978 | Briet et al. | 549/403 |
| 4,148,900 | 4/1979 | Doria et al. | 549/401 |

Primary Examiner—Nicky Chan
Attorney, Agent, or Firm—Browdy and Neimark

[57] ABSTRACT

The invention concerns [oxo-4-4H-[1]-benzopyran-8-yl]-alcanoic acids and their derivatives, their manufacture, represented by the formula.

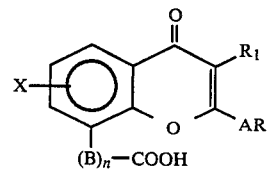

where AR is hydrogen, a phenyl radical which may or may not be substituted thenyl, furyl, naphthyl, a lower alkyl, cycloalkyl, aralkyl radical; B is a linear or branched lower alkyl radical, either saturated or ethylinically unsaturated; $R_1$ is hydrogen or a phenyl radical; X is hydrogen or a lower alkyl or alkoxy radical and n=1, as well as salts, esters, aminoesters and amides.

Compounds and their derivatives may be used as medicines, in particular in the control of tumors.

9 Claims, No Drawings

[OXO-4-4H-[1]-BENZOPYRAN-8-YL]ALCANOIC ACIDS, SALTS AND DERIVATIVES, THEIR MANUFACTURE AND MEDICINES CONTAINING THEM

This is a continuation of application Ser. No. 669,037 filed Nov. 6, 1984, now U.S. Pat. No. 4,602,034, which is a continuation of Ser. No. 442,191, filed Nov. 15, 1982, abandoned.

The invention concerns [oxo-4-4H-[1]-benzopyran-8-yl]alkanoic acids, certain of their salts and derivatives, their preparations, intermediate compounds necessary to produce them and some medicines containing them.

These compounds are represented by the formula:

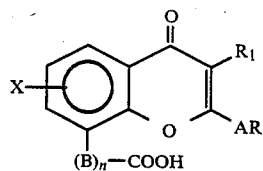
(I)

where AR is hydrogen, a phenyl radical which may or may not be substituted thenyl, furyl, naphthyl, a lower alkyl, cycloalkyl, aralkyl radical; B is a linear or branched lower alkyl radical, either saturated or ethylinically unsaturated; $R_1$ is hydrogen or a phenyl radical; X is hydrogen or a lower alkyl or alkoxy radical and $n=1$, as well as their alkaline metal salts, in particular sodium salts.

These acids may be prepared in accordance with the invention by one or other of the methods described below, which enable them to be prepared at good yield levels.

When it is the case that in formula 1 for the acids: $n=1$ and $B=CH_2$, the acids are prepared by hydrolysing a nitrile of the formula:

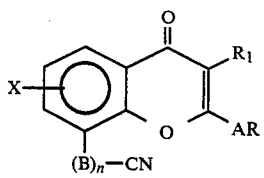
(II)

where AR, X and $R_1$ have the same meanings as before, in particular in a hot acid medium. The above nitriles are obtained by treating bromomethyl-8 benzopyranone-4 having the formula:

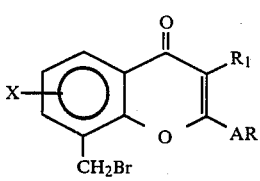
(III)

where X, AR and $R_1$ have the same meanings as before, with an alcaline cyanide. These nitriles are new intermediate compounds and, in this respect, are part of the invention.

When in formula I for acids: $n=1$ and $B=CH=CH$, it is also possible to react a bromomethyl-8 benzopyranone-4 of formula (III) with hexamethylenetetramine, and then condense the aldehyde obtained. When in formula I for the acids: $n=1$ and $B=CH=CH$, concentration is carried out with acetic anhydride in the presence of sodium acetate. [oxo-4-phenyl-2-4H-[1]-benzopyran-8-yl]carboxaldehyde is a new intermediate product. When AR=H and $R_1$=phenyl, the aldehyde obtained is condensed with tetraethyl diethylaminomethylenediphosphonate in the presence of sodium hydride. The corresponding acid is obtained by hydrolysis. [oxo-4-phenyl-3-4H[1]-benzopyran 8-yl] is new and is an intermediate product.

Where $n=1$ and B is a branched alkyl radical, in particular

the introduction of the branch is performed by converting the acid to an ester and then to the malonate which is alkylated and then hydrolised in the corresponding acid. When $n=1$ and B is $CH_2$—$CH_2$, bromomethyl-8 benzopyranone-4, having formula III, is initially made to react with the diethyl malonate in the presence of a base such as sodium hydride, the sodium alcoholate or sodium in an appropriate solvent. The substituted malonate obtained is then hydrolysed in the corresponding acid.

Malonates represented by the formulae:

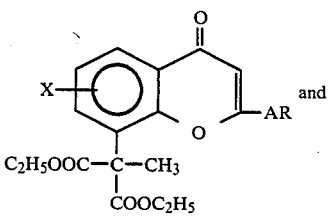
(IV)

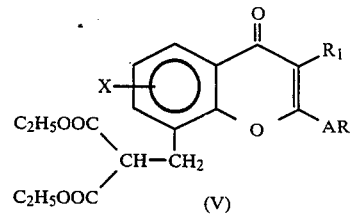
(V)

where X, AR and $R_1$ have the same meanings as before, are new intermediate compounds in the preparation of compounds covered by the invention.

Salts of alkaline metals from acids coming under the invention, in particular sodium salts are obtained by neutralising the above acids.

Derivatives of acids in the form of esters of the formula:

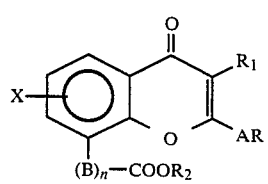
(VI)

where AR, B, X, $R_1$ and n have the same meanings as previously, $R_2$ being a lower alkyl or lower hydroxyalkyl radical prepared by esterification of the previous acids.

Aminoesters as in formula VI, where AR, B, $R_1$, X and n have the same meanings as before, $R_2$ being a lower dialkyl, lower dialkyl amino lower alkyl or morpholinoethyl radical are obtained by condensing the preceding acids with a halogen, preferably chloralkylaminodialkyl.

The amides derived from the acids represented by the formula:

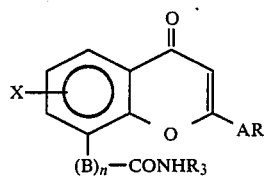

where AR, B and n have the same meanings as previously, $R_3$ being a dialkylaminoalkyl radical are obtained by condensing the esters of the acids having formula VI where $R_2$ is a lower alkyl radical, with a dialkylaminoalkylamine.

The salts of esters, aminoesters and amides with mineral or organic acids that are acceptable in human therapy are easily obtainable and simple to use.

The acids and their derivatives covered by the invention, and more particularly the substance in example 3 have exhibited worthwhile pharmacological properties as anti-tumour drugs. Pharmacological tests having been carried out on several types of tumours. Examples are:

P 388 lymphocytic leukemia: a test was carried out on CFD1 strain mice. 0.1 ml of ascetic fluid containing $10^6$ cells are implanted intraperitonally at day zero. The animals were treated i.p. from day 1 to day 9, with one injection per day and weighed on day 1 and day 5 (toxic day). The control value (median survival time) accepted was 9-14 days. Six mice were used per test (one test=one dose). A difference in weight of more than 4 g at day 5 between the test mice and the control mice was an indication of toxicity. The following ratio was determined:

$$\frac{T}{C} = \frac{\text{median survival of test mice}}{\text{median survival of control mice}}$$

A T/C <85% indicates toxicity. T/C between 85 and 120% indicates non-activity. T/C >120% indicates activity.

In this test, the substance in example 3, administered at the rate of 200 mg/kg gave T/C=195. Under the same conditions, 5-Fluorouracile, an anti-metabolite class of anti-cancer substance (antipyrimidine) gave T/C=185.

Carcinoma 38 of the colon: This test was carried out on B6C3F1 or BDF1 strain mice. A fragment of 70 mg of tumour was implanted sub-cutaneously at day zero. The animals were treated i.p. from day 2 to day 9 (2 injections). The accepted control value is the mean tumour weight situated between 400 and 2000 mg. 10 mice were used per test. The following ratio was determined:

$$\frac{T}{C} = \frac{\text{mean test tumour weight}}{\text{mean control tumour weight}}$$

Activity is indicated by T/C less than 42. As an example, the substance in example 3 gave the following results in the three cases: Administered doses T/C 200 mg/kg: 10; 200 mg/kg: 0; 50 mg/kg: 38.

The medicine contains, as its active ingredient, a compound covered by the invention, associated with an acceptable vehicle or pharmaceutical excipient, in a suitable form for oral, parenterale or intravenous administration.

Unit doses may be sugar-coated pills, tablets, capsules, gellules, phials or bottles. These dosage forms contain between 50 and 1000 mg of active ingredients.

As an example, the following compositions are to be found: Coated pill: active ingredient: 100 mg. Excipients: magnesium stearate, lactose, talcum, starch, alginic acid, hydroxypropylcellulose. Bottle: active ingredient: 1000 mg in freeze-dried form desolved in 20 ml of water for administration by injection.

Examples are given below illustrating the invention. They are not exhaustive.

EXAMPLE 1

[oxo-4-phenyl-2-4H[1]-benzopyran-8-yl]acetonitrile
$C_{17}H_{11}NO_2$ (formula 1), MW=261.26

A solution of 31 g (0.476 mole) of potassium cyanide in 150 ml of water is heated to 60°-70° C. A suspension of 75 g (0.238 mole) of bromomethyl-8-phenyl-2-4H-[1]-benzopyran-4-one in 965 ml of boiling ethanol is then added in fraction, and then boiled for 3 hours with a reflux condensor. The mixture is filtered hot and filtrate is placed in a refrigerator for 48 hours. The precipitate formed is centrifuged and dried. Weight obtained: 42 g (Yield 67.5%), IR: $\nu c=0$: 1640 cm$^{-1}$. $\delta$NMR (DMSO) compared with T.M.S. 2H at 4.45 (singlet), 1H at 7.05 (singlet), 8H from 7.15 to 8.6 (solid).

EXAMPLE 2

[oxo-4-phenyl-2-4H-[1]-benzopyran-8-yl]-acetic acid
$C_{17}H_{12}O_4$ (formula 2) MW=280.27

42 g (0.16 mole) of oxo-4-phenyl-2-4H-[1]-benzopyran-8-yl]acetonitrile are added to a mixture consisting of 117 ml of acetic acid and 117 ml of water. 117 ml of concentrated sulfuric acid are then added slowly and the mixture is refluxed for 3½ hours. After cooling, it is poured into 1.5 liters of iced water. The precipitate formed is centrifuged, and taken up in a 5% sodium bicarbonate solution at 50°-60° C. The remaining, slightly insoluble matter is filtered out and the filtrate acidified with concentrated hydrochloric acid. The beige-coloured precipitate is centrifuged, washed in water, dried and re-cristallised in alcohol. Weight obtained: 39.7 g (Yield 88.6%), MP$_G$: 234° C., IR: $\nu=0$ (pyrone): 1640 cm$^{-1}$; $\nu=0$ (acid): 1720 cm$^{-1}$, NMR (DMSO) $\delta$ en ppm compared with T.M.S. 2H at 4 (singlet), 1H at 7 (singlet), 8H from 7.3 to 8.3 (solid), 1H at 12.6 (exchangeable) with $D_2O$).

| Weight analysis | C % | H % | 0 % |
| --- | --- | --- | --- |
| Calculated: | 72.84 | 4.32 | 22.84 |
| Found: | 72.73 | 4.36 | |

EXAMPLE 3

(diethylamino-2-ethyl)[oxo-4-phenyl-2-4H-[1]-benzopyran-8-yl-]acetate $C_{23}H_{25}NO_4$ (formula 3) MW=379.39

21 g (0.075 mole) of [oxo-4-phenyl-2-4H-[1]-benzopyran-8-yl-]acetic acid are dissolved in 1.2 liters of ethanol. The mixture is removed from the heat and a solution of 4.2 g (0.075 mole) of potassium hydroxide in 75 cm3 of ethanol is added. This is stirred for 30 minutes at room-temperature, the alcohol evaporated, the solid residue is dried azeotropically with benzene, after which 370 ml of acetone added, plus a solution of 11 g (0.0813 mole) of diethylamino-2-chloro-1-ethane in 37 ml acetone. This is heated in a reflux condenser for four hours. The insoluble matter is filtered out when hot and the filtrate evaporated under vacuum. An oil is obtained which cristallises at room temperatures. IR: $\nu=0$ (ester): 1730 cm$^{-1}$, $\nu=0$ (pyrone): 1660 cm$^{-1}$.

Chlorhydrate: $C_{23}H_{26}ClNO_4$, MW=415.89, BP$_G$: 186° C. (isopropanol)

IR: $\nu c=0$ (ester): 1740 cm$^{-1}$, $\nu c=0$ (pyrone): 1660 cm$^{-1}$, $\nu NH^+$: band from 2400 to 2700 cm$^{-1}$, NMR (CDl$_3$) δ in ppm compared with T.M.S. 6H at 1.2 (triplet), 6H from 2.8 to 3.4 (solid), 2H at 4.15 (singlet), 2H at 4.6 (triplet, 1H at 6.8 (singlet), 8H from 7.2 to 8.3 (solid), 1H at 12.6 (exchangeable with D$_2$O).

| Weight analysis: | C % | H % | Cl % | N % | O % |
| --- | --- | --- | --- | --- | --- |
| Calculated: | 66.42 | 6.30 | 8.52 | 3.36 | 15.40 |
| Found: | 66.42 | 6.42 | 8.60 | 3.40 | |

EXAMPLE 4

(morpholinyl-4)-2-ethyl)[oxo-4-pphenyl-2-4H-[1]-benzopyran-8-yl]acetate $C_{23}H_{23}NO_5$ (formula 4), MW=393.38

This substance is prepared using the process in example 3 from 17.5 g (0.0625 mole) of [oxo-4-phenyl-2-4H-[1]-benzopyran-8-yl]acetic acid, 3.9 g (0.0625 mole) of potassium hydroxide and 11.3 g (0.0755 mole) of (chloro-2-ethyl)-4-morpholine. After isolation and treatment with gaseous HCl and re-cristallization in methanol, a white solid is obtained.

Chlorhydrate: $C_{23}H_{24}ClNO_3$, MW=429.88.

Weight obtained: 10.1 G (Yield: 37.3%, MP$_G$=193°-194° C. IR: $\nu c=0$ (ester): 1740 cm$^{-1}$, $\nu c=0$ (pyrone): 1640 cm$^{-1}$, $\nu NH^+$: band from 2300 to 2600 cm$^{-1}$;

NMR (DMSO) δ in ppm compared with T.M.S. 6H from 2.8 to 3.5 (solid), 4H to 3.7 to 4.1 (solid), 2H at 4.2 (singlet), 2H at 4.55 (triplet), 1H at 6.8 (singlet), 8H from 7.2 to 8.3 (multiplet), 1H at 12.5 (exchangeable with D$_2$O).

EXAMPLE 5

(dimethylamino-3 propyle)[oxo-4-phenyl-2-4H-[1]-benzopyran-8-yl]acetate $C_{22}H_{23}NO_4$ (formula 5), MW=365.38

This substance is prepared in accordance with the process in example 3 from 12.3 g (0.044 mole) of [oxo-4-phenyl-2-4H-[1]-benzopyran-8-yl]acetic acid, 2.74 g (0.044 mole) of potassium hydroxide and 6.45 g (0.053 mole) of dimethylamino-3-chloro-1-propane. A white solid is obtained after processing. Weight obtained : 10.5 g (Yield: 65.31%), MP$_G$: 112° C. (diisopropylether).

IR: $\nu c=0$ (ester): 1735 cm$^{-1}$, $\nu c=0$ (pyrone): 1645 cm$^{-1}$ NMR (CDCl$_3$) δ in ppm compared with T.M.S. 10H from 1.6 to 3.2 (multiplet), 4H from 3.9 to 4.2 (multiplet) 1H at 6.8 (singlet), 8H from 7.2 to 8.3 (multiplet).

Chlorhydrate: $C_{22}H_{24}ClNO_4$, MW=401.88, MP$_G$: 162°-164° C. (acetone).

| Weight analysis: | C % | H % | Cl % | N % | O % |
| --- | --- | --- | --- | --- | --- |
| Calculated: | 65.75 | 6.02 | 8.82 | 3.49 | 15.92 |
| Found: | 65.38 | 6.17 | 8.71 | 3.47 | |

EXAMPLE 6 ethyl[oxo-4-phenyl-2-4H-[1]-benzopyran-8-yl-]acetate $C_{19}H_{16}O_4$ (formula 6), NW=308

5.1 g (0.0175 mole) of [oxo-4-phenyl-2-4H-[1]-benzopyran-8yl]acetic acid are refluxed for 7 hours in 75 ml of absolute ethanol in the presence of 10 ml of concentrated sulphuric acid. The mixture is then put into a refigerator, the precipate formed is centrifuged, washed with a sodium bicarbonate solution and water. It is recrystallized in ethanol. Weight obtained: 4 g (Yield: 74%), MP$_K$: 140° C.

IR: $\nu c=0$ (ester); 1740 cm$^{-1}$, $\nu c=0$ (pyrone): 1645 cm$^{-1}$

EXAMPLE 7 methyl[oxo-4-phenyl-2-4H-[1]-benzopyran-8-yl-]acetate $C_{18}H_{14}O_4$ (formula 7), MW=294

This substance is prepared as in example 6 from 18 g (0.064 mole) of [oxo-4-phenyl-2-4H-[1]-benzopyran-8-yl]acetic acid, 260 ml of anhydrous methanol and 13 ml of concentrated sulphuric acid. Weight obtained: 18.1 g (Yield: 96%), MP$_K$: 168°-169° C. (methanol).

IR: $\nu c=0$ (ester): 1735 cm$^{-1}$, $\nu c=0$ (lactone): 1640 cm$^{-1}$.

NMR (CDCl$_3$) δ in ppm compared with TMS. 3H at 3.8 (singulet), 2H at 4.1 (singulet) 1H at 6.9 (singulet), 8H from 7.4 to 8.55 (multiplet).

EXAMPLE 8 sodium salt of [oxo-4-phenyl-2-4H-[1]-benzopyran-8-yl]acetic acid $C_{17}H_{11}O_4Na$, (formula 8), MW=302.24

The solution is prepared of 2.1 g (0.025 mole) of sodium bicarbonate in 400 ml of water. It is heated to 50° C. and 7 g (0.025 mole) of [oxo-4-phenyl-2-4H-[1]-benzopyran-8-yl]acetic acid are added. After the solid matter has completely dissolved, the liquid matter is allowed to cool to 30° C. and is poured into 2 liters of acetone. A white precitate forms which is centrifuged, rinsed of acetone and dried. Weight obtained: 6.2 g (Yield: 79.68%), MP$_G$=302°-304° C. (dimethylformanide). IR: $\nu c=0$ (pyrone): 1640 cm$^{-1}$.

| | Semihydrate MW = 311.24 | | | |
| --- | --- | --- | --- | --- |
| Weight analysis | C % | H % | O % | Na % |
| Calculated: | 65.54 | 3.85 | 23.13 | 7.38 |
| Found: | 65.60 | 3.88 | | |

EXAMPLE 9 hydroxy-2-ethyl[oxo-4-phenyl-2-4H-[1]-benzopyran-8-yl]acetate $C_{19}H_{16}O_5$ (formula 9), MW=324.32

4 g of paratoluenesulfonic acid and 300 ml of benzene are put into a reaction vessel. After elimination of the water, 28 g (0.1 mole) of [oxo-4-phenyl-2-4H-[1]-benzopyran-8-yl]acetic acid and 300 ml of ethylene glycol are added. This is heated for four hours in a reflux condenser to eliminate the water azyotropically. The orange solution obtained is concentrated under vacuum and the residue poured into 1.5 liter of iced water. The beige-coloured precipitate formed is centrifuged, washed with water and recrystallized in 300 ml of ethanol. Weight obtained: 23.5 g (Yield: 72.5%), $MP_G = 158°-159°$ C. IR: $vc=0$ (pyrone): 1640 cm$^{-1}$, $vc=0$ (ester): 1725 cm$^{-1}$, OH: 3400 cm$^{-1}$: MNR (CDCl$_3$) δ in ppm compared with TMS.

3H from 3.45 to 3.9: (multiplet, 1H exchangeable with D$_2$O), 4H from 3.9 to 4.4: (multiplet), 1H at 6.8: (singular), 8H from 7.3 to 8.3: (multiplet).

| Weight analysis: | C % | H % |
|---|---|---|
| Calculated: | 70.36 | 4.97 |
| Determined: | 70.26 | 4.74 |

EXAMPLE 10

N-[N'N'-diethylamino-2-ethyl][oxo-4-phenyl-2-4H-[1]-benzopyran-8-yl]acetamide $C_{23}H_{26}N_2O_3$ (formula 10), MW=378.43

A mixture of 14.8 g (0.048 mole) of ethyl[oxo-4-phenyl-2-4H-[1]-benzopyran-8-yl]acetate and 6.2 g (0.053 mole) of diethylamino-2 ethylamine is heated to 135°-140° C. for 5 hours. The mixture is then evaporated under vacuum and the residue is dissolved in hot hexane and then recrystallized in ethyl acetate. Weight obtained: 7.5 grams (Yield: 41.28%)

IR: $vc=0$ (pyrone and amide): 1640.60 cm$^{-1}$, $v$NH: 3300 cm$^{-1}$ Chlorhydrate $C_{23}G_{27}ClN_2O_3$, MW=414.93, $MP_G=216°-218°$ C. (ethanol).

| Weight analysis | C % | H % | N % |
|---|---|---|---|
| Calculated: | 66.57 | 6.56 | 6.75 |
| Determined: | 66.44 | 6.66 | 6.76 |

EXAMPLE 11

[oxo-4-(thenyl-2)-2-4H-[1]-benzopyran-8-yl]acetonitrile $C_{15}H_9NO_2S$, (formula 11), MW=267

Prepared as in example 1 from 69.5 g (0.215 mole) of bromomethyl-8-(thenyl-2)-2-4H-[1]-benzopyran-4-one and 28.4 g (0.42 mole) of potassium cyanide. Weight obtained: 21.7 g (Yield: 40%) $MP_K$: 184° C. (Ethanol).

IR: $vc=0$ (pyrone): 1645 cm$^{-1}$, $vc=N$: 2150 cm$^{-1}$. NMR (DMSO) δ ppm compared with TMS, 2H at 4.55 (singlet), 1H at 7 (singlet), 6H from 7.3 to 8.3 (multiplet).

EXAMPLE 12

[oxo-4-(thenyl-2)-2-4H-[1]-benzopyran-8-yl]acetic acid $C_{15}H_{10}O_4S$ (formula 12), MW=286.31

This preparation is prepared as in example 2 of 21.7 g (0.081 mole) of [oxo-4-thenyl-2)-2-4H-[1]-benzopyran-8-yl]acetonitrile. After treating with sodium bicarbonate, a substance is obtained which is recrystallized in dioxanne. Weight obtained: 13.9 g (Yield: 60%), $MP_G=247°-255°$ C.

IR: $vc=0$ (pyrone): 1630 cm$^{-1}$, $vc=0$ (acid): 1710 cm$^{-1}$, OH: 2400-2800 cm$^{-1}$, NMR (DMSO) δ in ppm compared with TMS, 2H at 4 (singlet), 1H at 7 (singlet), 6H from 7.3 to 8.2 (multiplet), 1H at 12 (solid exchangeable with D$_2$O).

EXAMPLE 13

Methyl [oxo-4-(thenyl-2)-2-4H-[1]-benzopyran-8-yl]acetate, $C_{16}H_{12}O_4S$, (formula 13), MW=300.32

Substance prepared as in example 7 from 10.2 g (0.035 mole) of [oxo-4-(thenyl-2)-2-4H-[1]-benzopyran-8-yl]acetic acid. Weight obtained: 7.7 g (Yield: 68.5%), $MP_G=168°-170°$ C. (methanol), IR: $vc=0$ (Pyrone): 1645 cm$^{-1}$, $vc=0$ (ester): 1720 cm$^{-1}$.

| Weight analysis: | C % | H % | S % |
|---|---|---|---|
| Calculated: | 63.98 | 4.03 | 10.68 |
| Determined: | 64.07 | 4.02 | 10.70 |

EXAMPLE 14

[Oxo-4-(thenyl-2)-4H-[1]-benzopyran-8-yl]acetate of (N-N diethylamino)-2-ethyl $C_{21}H_{23}NO_4S$ (formula 14), MW=385.45.

This substance is prepared as in example 3 from 9.6 g (0.036 mole) of [Oxo-4-(thenyl-2)-2-4H-[1]-benzopyran-8-yl]acetic acid, 2.2 g (0.033 mole) of potassium hydroxide and 5 g (0.033 mole) of chloro-2-N-N-diethylethylamine. Treatment produces an oil. Weight obtained: 12 g (Yield: 88%).

Chlorhydrate $C_{21}H_{24}ClNO_4S$. MW=421.92. $MP_G=210°-213°$ C. (ethanol).

IR: $v$NH+=2800-2400 cm$^{-1}$, $vc=0$ (ester)=1760 cm$^{-1}$, $vc=0$ (pyrone)=1640 cm$^{-1}$.

MNR (CDCl$_3$) δ in ppm compared with TMS, 6H at 1.15 (triplet, J=7 Hz), 6H from 2.7 to 3.5 (multiplet), 2H at 4.1 (singlet), 2H at 4.45 (triplet, J=6 Hz), 1H at 6.9 (singlet), 6H from 7.1 to 8 (multiplet), 1H at 10.6 (exchangeable with D$_2$O),

| Analysis | C % | H % | Cl % | N % | O % | S % |
|---|---|---|---|---|---|---|
| Calculated | 59.80 | 5.73 | 8.40 | 3.31 | 15.16 | 7.60 |
| Determined | 59.85 | 5.79 |  | 3.35 |  | 7.67 |

EXAMPLE 15

[Methyl-6-oxo-4-phenyl-2-4H-[1]-benzopyran-8-yl]acetonitrile $C_{18}H_{13}NO_2$ (formula 15), MW=275.

This substance is prepared as in example 1 from 16.4 g (0.05 mole) of bromomethyl-8-methyl-6-4H[1]-benzopyran-4-one and 6.5 g (0.01 mole) of potassium cyanide. Weight obtained: 11 g (Yield: 80%), $MP_K=255°$ C.

IR: $vc=0$ (pyrone): 1630 cm$^{-1}$, $v$CN: 2250 cm$^{-1}$.

EXAMPLE 16

[Methyl-6-oxo-4-phenyl-2-4H-[1]-benzopyran-8-yl]acetic acid $C_{18}H_{14}O_4$, (formula 16), MW=294

This substance is prepared as in example 2 from 11 g (0.04 mole) of [methyl-6-oxo-4-phenyl-2-4H-[1]-benzopyran-8-yl]acetonitrile. Weight obtained: 6.2 g (Yield: 53%), MP$_K$: 238°–239° C. (ethanol), IR: $vc=0$ (pyrone): 1640 cm$^{-1}$, $vc=0$ (acid) 1710 cm$^{-1}$. NMR (DMSO) δ in ppm compared with TMS: 3H at 2.4 (singlet), 1at 3.8 (solid exchangeable with D$_2$O) 2H at 4 (singlet), 1H at 7 (singlet), 7H from 7.4 to 8.3 (multiplet).

EXAMPLE 17

Methyl[methyl-6-oxo-4-phenyl-2-4H-[1]-benzopyran-8-yl]acetate C$_{19}$H$_{16}$O$_4$, (formula 17), MW=308

This substance is prepared as in example 7 from 84.7 g (0.288 mole) of [methyl-6-oxo-4-phenyl-2-4H-[1]-benzopyran-8-yl]acetic acid. Weight obtained: 75 g (Yield: 84.55%), MP$_K$: 228°–230° C. IR: $vc=0$ (ester) 1740 cm$^{-1}$, $vc=0$ (pyrone): 1638 cm$^{-1}$.

EXAMPLE 18

[Methyl-6-oxo-4-phenyl-[1]-benzopyran-8-yl]acetate of (N,N-diethylamino)-2-ethyl C$_{24}$H$_{27}$NO$_4$ (formula 18), MW=393.49

This substance is prepared as in example 3 from 8.5 g (0.029 mole) of [methyl-6-oxo-4-phenyl-2-4H-[1]-benzopyran-8-yl)acetic acid and 4.73 g (0.035 mole) of chloro-2-N,N-diethylethylamine, replacing acetone by DMF and heating for 2½ hours at 80° C. After evaporation of the DMF, the residue is dissolved in chloroform, washed with sodium hydroxide and then in water, dried, evaporated under vacuum and recrystallized in a hexane-toluene mixture. Weight obtained: 8.8 g (Yield: 77%), MP$_K$=120° C., IR: $vc=0$ (pyrone)=1655 cm$^{-1}$; $vc=0$ (ester)=1750 cm$^{-1}$, NMR (CDCl$_3$) 6H at 0.92 (triplet, J=7 Hz), 9H from 2.3 to 2.9 (multiplet), 2H at 3.97 (singlet), 2H at 4.2 (triplet, J=6 Hz), 1H at 6.8 (singlet), 7H from 7.2 to 8.1 (multiplet).

Chlorhydrate C$_{24}$H$_{28}$ClNO$_4$. MW=429.95, MP$_G$=188°–190° (ethanol-ether).

| Weight analysis | C % | H % | Cl % | N % | O % |
|---|---|---|---|---|---|
| Calculated | 64.07 | 6.56 | 8.25 | 3.26 | 14.89 |
| Determined | 64.34 | 6.35 | 8.27 | 3.46 | |

EXAMPLE 19

Diethyl[oxo-4-phenyl-2-4H-[1]-benzopyran-8-yl]-2, methyl-2-malonate C$_{23}$H$_{22}$O$_6$ (formula 19), MW=394

200 ml of ethyl carbonate are put into 3.26 g (0.068 mole) of 50% sodium hydride. The mixture is heated to 60° C. and 19 g (0.065 mole) of methyl[oxo-4-phenyl-2-4H-[1]-benzopyran-8-yl]acetate are added. It is then taken progressively to reflux temperature and after an hour a white precipitate is formed. Refluxing is continued for 2 hours and the mixture is then cooled to 20° C. and, at this temperature, a solution of 23 g of methyl iodide in 65 ml of dmethyl-formamide is added. This is left stirring overnight, the precipitate is centrifuge-separated and filtrate evaporated under vacuum, taken up in water and extracted with benzene. After drying and evaporating the solvent, the oil obtained is recrystallized in diisopropylether. Weight obtained: 19.3 g (Yield: 75%), MP$_K$=130° C. NMR (CCl$_4$) δ in ppm as compared with TMS, 6H at 1.2 (triplet), 3H at 2 (singlet), 4H at 4.15 (quartet), 1H at 6.85 (singlet), 8H from 7.3 to 8.4 multiplet).

EXAMPLE 20

[oxo-4-phenyl-2-4H-[1]-benzopyran-8-yl]-2 propionic acid C$_{18}$H$_{14}$O$_4$ (formula 20) MW=294

19 g (0.048 mole) of diethyl[oxo-4-phenyl-2-4H-[1]-benzopyran-8-yl]-2, methyl-2, malonate, 100 ml of acetic acid and 50 ml of concentrated hydrochloric acid are heated together in a reflux condenser for 7 hours. The mixture is cooled to room temperature and 50 ml of water added while stirring. The precipitate is filtered, washed with water and taken up in 500 ml of a 5% sodium bicarbonate solution. The insoluble matter is filtered off and acidified with concentrated HCl. Weight obtained: 4.1 g (28.9%). MP$_G$=216°–218° C. IR: $vc=0$ (pyrone): 1640 cm$^{-1}$, $vc=0$ (acid): 1740 cm$^{-1}$. NMR (DMSO) δ in ppm in comparison with TMS 3H at 1.65 (doublet), 1H at 3.8 (exchangeable with D$_2$O), 1H at 4.4 (quartet), 1H at 7.1 (singlet), 8H from 7.4 to 8.4 (multiplet).

| Weight analysis: | C % | H % |
|---|---|---|
| Calculated: | 73.46 | 4.79 |
| Determined: | 73.47 | 4.70 |

EXAMPLE 21

[Oxo-4-phenyl-2-4H-[1]-benzopyran-8-yl]-2-propionate of (N,N-diethylamino)-2-ethyl C$_{24}$H$_{27}$NO$_4$, (Formula 21), MW=393.46

This substance is prepared as in example 3 from 3.6 g (0.012 mole) of [oxo-4-phenyl-2-4H-[1]-benzopyran-8-yl]-2-propionic acid, 0.08 g (0.012 mole) of potassium hydroxide and 1.82 g (0.012 mole) of chloro-2-N,N-diethylethylamine. An oil is obtained.

Chlorhydrate C$_{24}$H$_{28}$ClNO$_4$, MW=429.91, MP$_G$=261°–3° C. (ethanol)

IR: $vNH\oplus$=2400–2800 cm$^{-1}$, $vc=0$ (ester)=1745 cm$^{-1}$, $vc=0$ (pyrone)=1660 cm$^{-1}$. NMR (CDCl$_3$) δ in ppm as compared with TMS, 6H at 1.2 (triplet J=7 Hz), 3H at 1.8 (doublet J=8 Hz), 6H from 2.4 to 3.3 (multiplet), 3H from 3.4 to 3.8 (multiplet), 1H to 6.9 (singlet), 8H from 7.2 to 8.4 (multiplet), 1H to 12.7 (exchangeable with D$_2$O).

| Analysis | C % | H % | Cl % | N % | O % |
|---|---|---|---|---|---|
| Calculated | 67.04 | 6.56 | 8.25 | 3.26 | 14.89 |
| Determined | 66.88 | 6.52 | | 3.20 | |

EXAMPLE 22

Diethyl[methyl-6-oxo-4-phenyl-2-4H-[1]-benzopyran-8-yl]-2-methyl-2, malonate C$_{24}$H$_{24}$O$_6$ (formula 22) MW=408.45

This substance is prepared as in example 19 from 31.3 g (0.1 mole) of methyl [methyl-6-oxo-4-phenyl-2-4H-[1]-benzopyran-8-yl]acetate, 325 ml of ethyl carbonate, 5.39 g (0.11 mole) of 50% sodium hydride and 37.8 g of methyl iodide. Weight obtained: 32.3 g (Yield: 77.8%), MP$_K$=147°–148° C. (diisopropylether). MNR (CDCl$_3$) δ in ppm as compared with TMS, 6H at 1.2 (triplet), 3H at 2.05 (singlet), 3H at 2.5 (singlet), 4H at 4.2 (quartet), 1H at 6.8 (singlet), 7H from 7.2 to 8 (multiplet).

EXAMPLE 23

[Methyl-6-oxo-4-phenyl-2-4H-[1]-benzopyran-8-yl]-2, propionic acid $C_{19}H_{16}O_4$ (formula 23), MW=303.32

This substance is prepared as in example 20 from 32 g (0.078 mole) of diethyl[methyl-6-oxo-4-phenyl-2-4H-[1]-benzopyran-8-yl]-2 methyl-2-malonate. Weight obtained: 8.5 g (Yield: 35%). $MP_G$=232°–234° C. (ethanol-water). NMR (DMSO) δ in ppm as compared with TMS, 3H at 1.6 (doublet), 3H at 2.4 (singlet), 1H at 4.3 (quartet), 1H at 4.6 (extended solid exchangeable with $D_2O$), 1H at 7 (singlet), 7H at 7.4 to 8.3 (multiplet).

| Weight analysis: | C % | H % |
| --- | --- | --- |
| Calculated: | 74.01 | 5.23 |
| Determined: | 74.04 | 5.21 |

EXAMPLE 24

[Oxo-4-phenyl-2-4H-[1]-benzopyran-8-yl]carboxaldehyde $C_{16}H_{10}O_3$ (formula 24), MW=250.26

Method A 37.2 g (0.118 mole) of bromomethyl-8-phenyl-2-4H-[1]-benzopyran-4-one, are put into a reaction vessel with 27.6 g (0.197 mole) of hexamethylene tetramine and 400 ml of chloroform. The mixture is heated for 2 h in a reflux condenser, the chloroform is evaporated under vacuum and 515 ml of acetic acid are added. The mixture is then heated for 2 h under reflux and then, after filtration and the addition of 67.5 ml of concentrated hydrochloric acid, refluxing is continued for 30 minutes. The mixture is allowed to stand overnight. After evaporation under vacuum, the residue is recrystallized in the water/acetic acid mixture. Weight obtained: 11.6 g (Yield: 39.3%), $MP_K$: =190° C. IR: υc=0 (pyrone): 1650 cm$^{-1}$, υc=0 (aldehyde): 1710 cm$^{-1}$. NMR (DMSO) δ in ppm compared with TMS, 1H at 7.2 (singlet), 8H from 7.5 to 8.5 (multiplet), 1H at 10.7 singlet).

Method B 10.85 g (0.043 mole) of hydroxymethyl-8-phenyl-2-4H[1]-benzopyran-4-one, are put in a reaction vessel with 525 ml of chloroform and 11.21 g (0.129 mole) of activated $MNO_2$. This is then refluxed for 6 hours. The solid is filtered while hot, brought to the boil again with 500 ml of chloroform after which the chloroform solutions are mixed together and concentrated under vacuum. The solid obtained is recrystallized in the water/acetic acid mixture. Weight obtained: 6.1 g (Yield: 56.7%). Hydroxymethyl-8-phenyl-2-4H-[1]-benzopyran-4-one is obtained as follows: 13.1 g (0.041 mole) of bromomethyl-8-phenyl-2-4H-[1]-benzopyran-4-one are put into 104 ml of dioxanne and 104 ml of a 5% aqueous solution of sodium bicarbonate. The mixture is heated for 2 hours under reflux, concentrated under vacuum and the residue taken up in 300 ml of water. The precipitate obtained is centrifuged, dried and recrystallized in methanol. Weight obtained: 8 g (Yield: 77%), $MP_G$=175°–177° C. IR: υc=0 (pyrone): 1640 cm$^{-1}$, υOH: 3400 cm$^{-1}$. NMR (DMSO) δ in ppm compared with TMS, 2H at 5 (singlet), 1H at 5.45 (solid unchangeable by $D_2O$), 1H at 7 (singlet), 8H from 7.3 to 8.3 (multiplet).

| Analysis: | C % | H % |
| --- | --- | --- |
| Calculated: | 76.17 | 4.80 |
| Determined: | 76.54 | 4.60 |

EXAMPLE 25

[Oxo-4-phenyl-2-4H-[1]-benzopyran-8-yl]-3-propenoic acid $C_{18}H_{12}O_4$ (formula 25) MW: 292.28

A mixture of 15.8 g (0.06 mole) of [oxo-4-phenyl-2-4H-[1]-benzopyran-8-yl]carboxaldehyde, 12 ml of acetic anhydride and 5.3 g (0.064 mole) of anhydrous sodium acetate are heated to 140°–145° C. for 8 hours. After cooling, the material is taken up in hot water and the precitate obtained is centrifuged and washed with water, then brought to boiling point in a 5% sodium bicarbonate solution, insoluble matter is filtered off and, using hydrochloric acid to acidify the solution, a precipitate is obtained which is recrystallized in the water/acetic acid mixture. Weight obtained: 9.7 g (Yield: 52.5%); $MP_G$: 263°–265° C. IR: υc=0 (pyrone): 1640 cm$^{-1}$, υc=0 (acid): 1710 cm$^{-1}$. NMR (DMSO) δ in ppm compared with TMS. 1H at 3.8 (solid exchangeable with $D_2O$), 1H at 6.9 (J=15 Hz, duplet), 1H at 7.1 (singlet).

EXAMPLE 26

Diethylamino-2-ethyl[oxo-4-phenyl-2-4H-[1]-benzopyran-8-yl]-3-propenoate, $C_{24}H_{25}NO_4$ (formula 26) MW: 391.42

This substance is prepared as in example 3 from 3.4 g (0.011 mole) of [oxo-4-phenyl-2-4H-[1]-benzopyran-8-yl]-3-propenoic acid, 0.77 g (0.011 mole) of potassium hydroxide and 1.9 g (0.14 mole) of diethylamino-2-chloro-1-ethane. Weight obtained: 2.6 g (Yield: 60.3%), $MP_K$: 84° C. (hexane).

IR: υc=0 (pyrone): 1640 cm$^{-1}$, υc=0 (ester): 1720 cm$^{-1}$. NMR (CDCl$_3$) δ in ppm compared with TMS. 6H at 1.1 (triplet), 6H from 2.4 to 3 (multiplet), 2H at 4.4 (triplet), 1H at 6.8 (duplet, J: 15 Hz), 1H at 7 (singlet), 9H from 7.2 to 8.4 (multiplet).

Chlorhydrate $C_{24}H_{26}ClNO_4$, MW=427.92, $MP_G$=194°–196° C. (isopropanol).

| Weight analysis: | C % | H % | Cl % | N % |
| --- | --- | --- | --- | --- |
| Calculated: | 67.36 | 6.12 | 8.29 | 3.27 |
| Determined: | 67.22 | 6.07 | 8.16 | 3.21 |

EXAMPLE 27

(Morpholinyl-4)-2-ethyl[oxo-4-phenyl-2-4H-[1]-benzopyran-8-yl]-3-propenoate, $C_{24}H_{23}NO_5$ (formula 27), MW=405.4

This substance is prepared as in example 3 from 8.5 g (0.03 mole) of [oxo-4-phenyl-2-4H-[1]-benzopyran-8-yl]-3-propenoic acid, 1.92 g (0.03 mole) of potassium hydroxide and 5.25 g (0.035 mole) of (chloro-2-ethyl)-4-morpholine. Weight obtained: 9.5 g (Yield: 78.1%), $MP_K$=126° C. (acetone).

IR: υc=0 (pyrone): 1640 cm$^{-1}$, υc=0 (ester): 1720 cm$^{-1}$. NMR (CDCl$_3$) δ in ppm compared with TMS, 6H from 2.5 to 3 (multiplet), 4H from 3.7 to 4 (multiplet), 2H at 4.5 (triplet), 1H at 6.8 (duplet J=15 Hz), 1H at 7 (singlet), 9H from 7.4 to 8.6 (multiplet).

Chlorhydrate C₂₄H₂₄ClNO₅, MW=441.9, MP_G=243°-5° C.

| Analysis: | C % | H % | Cl % | N % |
|---|---|---|---|---|
| Calculated: | 65.23 | 5.47 | 8.02 | 3.17 |
| Determined: | 65.10 | 5.38 | 8.05 | 3.08 |

EXAMPLE 28

[(Methoxy-3-phenyl)-2-oxo-4-4H-[1]-benzopyran-8-yl]acetonitrile C₁₈H₁₃NO₃ (formula 28), MW=291.31.

This substance is prepared as in example 1 from 23.9 g (0.066 mole) of (bromomethyl)-8-(methoxy-3-phenyl)-2-4H-[1]-benzopyranone-4 and 9.1 g of potassium cyanide, to obtain 9.3 g of the substance with a yield of 46%. MP_K=170° C. IR: $\nu c=0=1650$ cm⁻¹. NMR (DMSO), 3H at 3.9 (singlet), 2H at 4.5 (singlet), 8H from 6.9 to 8.3 (multiplet).

EXAMPLE 29

[(Methoxy-3-phenyl)-2-oxo-4-4H-[1]-benzopyran-8-yl]acetic acid C₁₈H₁₄O₅ (formula 29), MW=310.31

This substance is prepared as in example 2 from 9.1 g (0.031 mole) of [(methoxy-3-phenyl)-2-oxo-4-4H-[1]-benzoyran-8-yl]-acetonitrile. Weight obtained: 2.2 g. MP_G=238°-241° (MiBK), IR: $\nu c=0$ (pyrone)=1635 cm⁻¹; $\nu c=0$ (acid)=1710 cm⁻¹. NMR (DMSO), 1H at 3.4 (exchangeable with D₂O), 3H at 3.9 (singlet), 2H at 4.02 (singlet), 1H at 7.1 (singlet), 7H from 7.1 to 8.1 (multiplet).

| Weight analysis: | C % | H % | O % |
|---|---|---|---|
| Calculated: | 69.67 | 4.55 | 25.78 |
| Determined: | 69.91 | 4.61 | |

EXAMPLE 30

(Methoxy-6-oxo-4-phenyl-2-4H-[1]-benzopyran-8-yl)acetonitrile C₁₈H₁₃NO₃, (formula 30), MW=291.31

This substance is prepared as in example 1 from 30 g (0.087 mole) of bromomethyl-8-methoxy-6-phenyl-2-4H-[1]-benzopyranone-4 and 11.9 g of potassium cyanide. Since the substance is insoluble when hot, it is not filtered when hot but is cooled, filtered cold, washed water and dried. Weight obtained: 15.9 g (Yield: 62%), MP_K=270° C., IR: $\nu c=0=1635$ cm⁻¹. The substance is not soluble enough to obtain an NMR spectrum.

EXAMPLE 31

(Methoxy-6-oxo-4-phenyl-2-4H-[1]-benzopyran-8-yl)acetic acid C₁₈H₁₄O₅ (formula 31) MW=310.31

This substance is prepared as in example 2 from 8 g (0.027 mole) of (methoxy-6-oxo-4-phenyl-2-4H-[1]-benzopyran-8-yl)acetonitrile. Weight obtained: 3.7 g, IR: $\nu c=0$ (pyrone)=1630 cm⁻¹; $\nu c=0$ (acid): 1720 cm⁻¹ $\nu OH=2400$ to 3500 cm⁻¹. The NMR shows that a mixture of the substance in the title and (hydroxy-6-oxo-4-phenyl-2-4H-[1]-benzopyran-8-yl)acetic acid (formula 32) has been obtained. This mixture is used as such in the following example.

EXAMPLE 32

(Methoxy-6-oxo-4-phenyl-2-4H-[1]-benzopyran-8-yl)acetate of (N,N-diethylamino)-2-ethyl C₂₄H₂₇NO₅, (formula 33) MW=409.49

This substance is prepared as in example 3 from 3.5 g of the acid mixture from example 31 and 1.84 g (0.013 mole) of chloro-2-N,N-diethylethylamine, replacing acetone by DMF, and heating for 2½ hours at 80° C. After evaporation, the solid is taken up in CH₂Cl₂, washed with N sodium hydroxide, then with water, dried and evaporated under vacuum. Weight obtained: 1.4 g. NMR (CDCl₃), 6H at 0.95 (triplet, J=7 Hz), 6H from 2.3 to 2.8 (multiplet), 3H at 3.9 (singlet), 2H at 3.96 (singlet), 2H at 4.2 (triplet, J=6 Hz), 1H at 6.8 (singlet), 7H from 7.1 to 8.1 (multiplet).

EXAMPLE 33

[(Dimethoxy-3,4-phenyl)-2-oxo-4-4H-[1]-benzopyran-8-yl]acetonitrile C₁₉H₁₅NO₄ (formula 34) MW=321.34

This substance is prepared as in example 1 from 30 g (0.080 mole) of (bromomethyl)-8-(dimethoxy-3,4-phenyl)-2-4H-[1]-benzopyranone-4 and 11 g of potassium cyanide. Weight obtained: 10.5 g (Yield: 40%). MP_K=226° C., IR: $\nu c=0$ (pyrone)=1650 cm⁻¹; $\nu c=N=2260$ cm⁻¹. The substance is not soluble and apt to obtain an NMR spectrum.

EXAMPLE 34

[(dimethoxy-3,4-phenyl)-2-oxo-4-4H-[1]-benzopyran-8-yl]acetic acid C₁₉H₁₆O₆ (formula 35) MW=340.34.

This substance is prepared as in example 2 from 10.2 g (0.032 mole) of [(dimethoxy-3,4-phenyl)-2-oxo-4-4H-[1]-benzopyran-8-yl]acetonitrile. Weight obtained: 3.9 g, MP_G=250°-254° (AcOH), IR: $\nu c=0$ (pyrone)=1645 cm⁻¹; $\nu c=0$ (acid)=1720 cm⁻¹. NMR (DMSO), 3H at 3.83 (singlet), 3H at 3.9 (singlet), 2H at 4.03 (singlet), 7H from 6.8 to 8.1 (multiplet), 1H at 12 (exchangeable with D₂O).

| Weight analysis: | C % | H % | O % |
|---|---|---|---|
| Calculated: | 67.05 | 4.74 | 28.21 |
| Determined: | 67.16 | 4.68 | |

EXAMPLE 35

Diethyl[(Oxo-4-phenyl-2-4H-[1]-benzopyran-8-yl)methyl]-2-propanedioate C₂₃H₂₂O₆ (formula 36) MW=390.24

Starting from a suspension of 2.3 g (0.1 mole) of sodium pellets in 100 ml of anhydrous benzene, 15.6 g (0.1 mole) of diethyl propanedioate is added at room temperature and heated for 5 hours in a reflux condenser, then left for 12 hours with stirring at room temperature. A solution of 31.5 g (0.1 mole) of bromomethyl-8-phenyl-2-4H-[1]-benzopyranone-4 in 300 ml of benzene is then added. The mixture is heated for 7 hours with reflux. After filtration and evaporation of the solvent, a white solid is isolated which is recrystallized. Weight obtained: 26 g (Yield: 66%), MP_G=87°-90° C. (ethanol), IR: $\nu c=0$ (ester)=1740 cm⁻¹, $\nu c=0$ (pyrone)=1650 cm⁻¹.

EXAMPLE 36

[Oxo-4-phenyl-2-4H-[1]-benzopyran-8-yl]-3-propionic acid $C_{18}H_{14}O_4$ (formula 37), MW=294.29

A solution of 26 g (0.066 mole) of diethyl[(oxo-4phenyl-2-4H-[1]benzopyran-8-yl)methyl]-2-propanedioate is heated in a reflux condenser for 7 hours with 93 ml of acetic acid and 46 ml of concentrated hydrochloric acid. The reacting mixture is poured into 800 ml of water and, after filtration, treated with 5% sodium bicarbonate solution. 10.5 g of the substance are obtained (Yield: 53%). $MP_G$=201°-202° C. (acetone/ethanol) IR: $\nu$OH (acid)=2800-3300 cm$^{-1}$ $\nu$c=0 (acid)=1740 cm$^{-1}$, $\nu$c=0 (pyrone)=1640 cm$^{-1}$. NMR (CDCl$_3$) $\delta$ in ppm compared with TMS, 2H at 2.6 (triplet J=7 Hz), 2H at 3.2 (triplet J=7 Hz), 1H at 7 (singlet), 8H from 7.2 to 8.2 (multiplet), 1H at 12.1 (exchangeable with D$_2$O).

| Analysis: | C % | H % | O % |
|---|---|---|---|
| Calculated: | 73.46 | 4.80 | 21.74 |
| Determined: | 73.52 | 4.55 | |

EXAMPLE 37

[(Furyl-2)-2-oxo-4-4H-[1]-benzopyran-8-yl]acetonitrile $C_{15}H_9NO_3$ (formula 38), MW=251.22

This substance is prepared as in example 1 from 23.4 g (0.077 mole) of bromomethyl-8-(furyl-2)-2-4H-[1]-benzopyranone-4 and 10 g (0.154 mole) of potassium cyanide. Weight obtained: 15.5 g (Yield: 83%). $MP_K$=195° C. (ethanol). IR $\nu$c=N=2250 cm$^{-1}$, $\nu$c=0 (pyrone): 1650 cm$^{-1}$.

EXAMPLE 38

[(furyl-2)-2-oxo-4-4H-[1]-benzopyran-8-yl]-acetic acid $C_{15}H_{10}O_5$ (formula 39), MW=270.23

This substance is prepared as in example 2 from 16 g (0.063 mole) of [(furyl-2)-2-oxo-4-4H-[1]-benzopyran-8-yl]acetonitrile. Weight obtained: 8.5 g (Yield: 49%). $MP_G$=240°-2° C. IR: OH=2800-3200 cm$^{-1}$, $\nu$c=0 (acid)=1720 cm$^{-1}$, $\nu$c=0 (pyrone)=1650 cm$^{-1}$. NMR (DMSO) $\delta$ in ppm compared with TMS, 2H at 4 (singlet), 1H at 6.7 (singlet), 1H from 6.8 to 7 (multiplet), 5H from 7.3 to 8.1 (multiplet), 1H at 12.6 (exchangeable with D$_2$O).

| Analysis: | C % | H % | O % |
|---|---|---|---|
| Calculated: | 66.67 | 3.73 | 29.60 |
| Determined: | 66.81 | 3.74 | |

EXAMPLE 39

[(Methyl-4-phenyl)-2-oxo-4-4H-[1]-benzopyran-8-yl]acetonitrile $C_{18}H_{13}NO_2$ (formula 40), MW=275.30

This substance is prepared as in example 1 from 33 g (0.1 mole) of bromomethyl-8-(methyl-4-phenyl-)-2-4H-[1]-benzopyranone-4 and 13 g (0.2 mole) of potassium cyanide. Weight obtained: 23.5 g (Yield: 85.5%). $MP_K$=190° C.

IR: $\nu$c=N=2160 cm$^{-1}$, $\nu$c=0 (pyrone)=1640 cm$^{-1}$.

EXAMPLE 40

[(methyl-4-phenyl-)-2-oxo-4-4H-[1]-benzopyran-8-yl]acetic acid $C_{18}H_{14}O_4$ (formula 41), MW=294.29

This substance is prepared as in example 2 from 23.5 g (0.085 mole) of [(methyl-4-phenyl)-2-oxo-4-4H-[1]-benzopyran-8-yl]acetonitrile. After treatment with sodium bicarbonate and recrystallization in acetic acid, 15 g of the substance are obtained. (Yield: 59%. $MP_G$=250-252° C.

IR: $\nu$OH=2800-3200 cm$^{-1}$, $\nu$c=0 (acid)=1720 cm$^{-1}$, $\nu$c=0 (pyrone)=1630 cm$^{-1}$. NMR (DMSO) $\delta$ in ppm compared with TMS, 3H at 2.2 (singlet), 2H at 4 (singlet), 1H at 7 (singlet), 7H from 7.2 to 8.1 (multiplet) 1H at 12.7 (exchangeable with D$_2$O).

| Analysis: | C % | H % | O % |
|---|---|---|---|
| Calculated: | 73.46 | 4.80 | 21.74 |
| Determined: | 73.77 | 4.94 | |

EXAMPLE 41

[(Methyl-4-phenyl)-2-oxo-4-4H-[1]-benzopyran-8-yl]acetate of (N,N-diethylamino)-2ethyl, $C_{24}H_{27}NO_4$ (formula 42), MW=393.46

This substance is prepared as in example 3 from 16.4 g (0.0557 mole) of [(methyl-4-phenyl)-2-oxo-4-4H-[1]-benzopyran-8-yl]acetic acid, 3.67 g (0.0557 mole) of potassium hydroxide and 8.27 g (0.061 mole) of chloro-2-N,N-diethylethylamine. 15 g (Yield: 70%) of a white solid are obtained. $MP_G$=87°-89° C. (diisopropylether).

Chlorhydrate $C_{24}H_{28}ClNO_4$, MW=429.91, $MP_G$=175°-177° C. (ethanol), IR: $\nu$NH+=2400-2800 cm$^{-1}$, $\nu$c=0 (ester)=1750 cm$^{-1}$, $\nu$c=0 (pyrone)=1640 cm$^{-1}$. RMN (CDCl$_3$) $\delta$ in ppm compared with TMS, 6H at 1.3 (triplet, J=7 Hz), 3H at 2.5 (singlet), 6H from 2.7 to 3.4 (multiplet), 2H at 4.2 (singlet), 2H at 4.7 (triplet, J=6 Hz), 1H at 6.8 (singlet), 7H from 7.2 to 8.4 (multiplet), 1H at 12.7 (exchangeable with D$_2$O).

| Analysis: | C % | H % | Cl % | N % | O % |
|---|---|---|---|---|---|
| Calculated: | 67.04 | 6.56 | 8.25 | 3.26 | 14.89 |
| Determined: | 67.30 | 6.67 | | 3.36 | |

EXAMPLE 42

[(Naphtyle-2-)-2-oxo-4-4H-[1]-benzopyran-8-yl]acetonitrile $C_{21}H_{13}NO_2$ (formula 43), MW=311.31

This substance is prepared as in example 1 from 61 g (0.167 mole) of bromomethyl-8-naphtyl-2)-2-4H-[1]-benzopyranone-4 and 21.8 g (0.344 mole) of potassium cyanide. 43 g (yield: 84%) are obtained. $MP_K$=189° C. (ethanol).

IR: $\nu$c=N=2260 cm$^{-1}$, $\nu$c=0 (pyrone)=1660 cm$^{-1}$.

EXAMPLE 43

[(Naphtyl-2)-2-oxo-4-4H-[1]-benzopyran-8-yl]acetic acid $C_{21}H_{14}O_4$ (formula 44), MW=330.32.

This substance is prepared as in example 2 from 43.5 (0.14 mole) of [(naphtyl-2)-2-oxo-4-4H-[1]-benzopyran-8-yl]acetonitrile. By recristallizing in acetic acid, 29 g of substance are obtained (yield: 62.7%). $MP_G=225°-228°$ C., IR=$\nu OH=2400-2800$ cm$^{-1}$, $\nu c=O$ (acid)=1720 cm$^{-1}$, $\nu c=O$ (pyrone)=1640 cm$^{-1}$. NMR (DMSO) δ in ppm compared with TMS, 2H at 4 (singlet), 1H at 7.1 (singlet), 10H from 7.2 to 8.2 (multiplet), 1H at 12.6 (exchangable with D$_2$O).

| Analysis: | C % | H % | O % |
|---|---|---|---|
| Calculated: | 76.35 | 4.27 | 19.38 |
| Determined: | 76.25 | 4.15 | |

EXAMPLE 44

[(Methoxy-4-phenyl)-2-oxo-4-4H-[1]-benzopyran-8-yl]actonitrile $C_{18}H_{13}NO_3$ (formula 45), MW=291.28

This substance is prepared as in example 1 from 34.5 g (0.1 mole) of bromomethyl-8-(methoxy-4-phenyl)-2-4H-[1]-benzopyranone-4 and 13 g (0.2 mole) of potassium cyanide. 25.3 g are obtained (yield: 87%). $MP_K=190°$ C. (ethanol), IR: $\nu c=N=2250$ cm$^{-1}$, $\nu c=O$ (pyrone)=1640 cm$^{-1}$.

EXAMPLE 45

[(Methoxy-4-phenyl)-2-oxo-4-4H-[1]-benzopyran-8-yl]acetic acid $C_{18}H_{14}O_5$, (formula 46), MW32 310.29

This substance is prepared as in example 2 from 25.3 g (0.087 mole) of [(methoxy-4-phenyl)-2-oxo-4-4H-[1]-benzopyran-8-yl]acetonitrile. Weight obtained: 23.6 g (yield: 87.4%). $MP_G=228°-232°$ C. (acetic acid). IR: $\nu OH=2400-2800$ cm$^{-1}$, $\nu c=O$ (acid)=1720 cm$^{-1}$, $\nu c=O$ (pyrone)=1640 cm$^{-1}$. NMR (DMSO) δ en ppm compared with TMS, 3H at 3.9 (singlet), 2H at 4.1 (singlet), 8H from 7 to 8.3 (multiplet), 1H at 12.7 (exchangable with D$_2$O).

| Analysis: | C % | H % | O % |
|---|---|---|---|
| Calculated: | 69.67 | 4.55 | 25.78 |
| Determined: | 69.64 | 4.58 | |

EXAMPLE 46

[(Methoxy-4-phenyl)-2-oxo-4-4H-[1]-benzopran-8-yl]acetate of (N,N-diethylamino)-2-ethyl, $C_{24}H_{27}NO_5$ (formula 47), MW=409.46

This substance is prepared as in example 3 from 17.3 g (0.0557 mole) of ([methoxy-4-phenyl)-2-oxo-4-4H-[1]-benzopyran-8-yl]-acetic acid, 3.67 g (0.0557 mole) of potassium and 8.27 (0.061 mole) of chloro-2-N,N-diethylethylamine. After processing, a solid is obtained which is recrystallized in di-isopropylether. Weight obtained: 16 g (yield: 70%). $MP_K=120°$ C.

Chlorhydrate $C_{24}H_{28}ClNO_5$, MW=445.91, $MP_G=161°-163°$ C., IR: $\nu NH+=2400-2800$ cm$^{-1}$, $\nu c=O$ (ester)=1750 cm$^{-1}$, $\nu c=O$ (pyrone): 1640 cm$^{-1}$. NMR (CDCl$_3$) δ in ppm compared with TMS, 6H at 1.3 (triplet, J=7 Hz), 6H from 2.8 to 3.4 (multiplet), 3H at 3.95 (singlet), 2H at 4.2 (singlet), 2H at 4.65 (triplet, J=6 Hz), 1H at 6.8 (singlet), 7H from 7 to 8.2 (multiplet), 1H at 12.7 (exchangable with D$_2$O).

| Analysis: | C % | H % | Cl % | N % | O % |
|---|---|---|---|---|---|
| Calculated: | 64.64 | 6.33 | 7.95 | 3.14 | 17.94 |
| Determined: | 64.50 | 6.41 | | 3.02 | |

EXAMPLE 47

[Cyclohexyl-2-oxo-4-4H-[1]-benzopyran-8-yl]acetonitrile $C_{17}H_{17}NO_2$ (formula 48) MW=267.33

This substance is prepared as in example 1 from 15.2 g (0.047 mole) of bromo-methyl-8-cyclohexyl-2-4H-[1]-benzopyranone-4 and 6.2 g (0.095 mole) of potassium cyanide. When the reaction is completed, the substance is evaporated under vacuum, taken up with water, extracted with chloroform, dried and evaporated under vacuum. Weight obtained: 12.4 g (yield: 98%) (oil). IR: $\nu c=N=2240$ cm$^{-1}$; $\nu c=O$ (pyrone)=1650 cm$^{-1}$ NMR (CDCl$_3$), 11H from 1.0 to 3.0 (multiplet), 2H at 3.9 (singlet), 1H at 6.2 (singlet), 2H from 7.2 to 7.9 (multiplet), 1H at 8.15 (double duplet, J$_1$=8 Hz, J$_2$=2 Hz).

EXAMPLE 48

[Oxo-4-(phenylmethyl)-2-4H-[1]-benzopyran-8-yl]acetonitrile $C_{18}H_{13}NO_2$ (formula 49), MW=275.31

This substance is prepared as in example 1 from 47 g (0.143 mole) of bromomethyl-8-(phenylmethyl-2-4H-[1]-benzopyranone-4 and 18.5 g (0.284 mole) of potassium cyanide. After filtration while hot it is evaporated under vacuum and recristallized in an ethanol/water mixture. Weight obtained: 7.1 g (yield: 18%), $MP_K=100°$ C. IR: $\nu c=N=2240$ cm$^{-1}$; $\nu c=O$ (pyrone)=1640 cm$^{-1}$. NMR (CDCl$_3$), 2H at 3.83 (singlet), 2H at 3.97 (singlet), 1H at 6.2 (singlet), 7H from 7.2 to 7.8 (multplet), 1H at 8.2 (double duplet, J$_1$=8 Hz, J$_2$=2 Hz).

EXAMPLE 49

Oxo-4-phenyl-3-4H-[1]-benzopyran carboxaldehyde-8 $C_{16}H_{10}O_3$ (formula 50) MW=250.26

This substances is prepared as in example 24 from 88.2 g (0.28 mole) of bromo-methyl-8-phenyl-3-4H-[1]-benzopyranone-4 with the following differences: after adding, the hydrochloric acid, no heat is applied but the mixture is shaken overnight at ambient temperature and then filtered to remove insoluble substances. The filtrate is diluted with water and the precipitate thus obtained is filtered. Weight obtained: 52.4 g (yield: 74%). $MP_K=162°$ C. (AcOEt), IR: $\nu c=O$ (pyrone)=1650 cm$^{-1}$, $\nu c=O$ (aldehyde)=1700 cm$^{-1}$. NMR (CDCl$_3$) 6H from 7.2 to 7.8 (multiplet), 1H at 8.12 (singlet), 1H at 8.3 (double duplet, J$_1$=8 Hz, J$_2$=2 Hz), 1H at 8.6 (double duplet, J$_1$=8 Hz, J$_2$=2 Hz), 1H at 10.7 (singlet).

EXAMPLE 50

(Cyclohexyl-2-oxo-4-4H-[1]-benzopyran-8-yl)acetic acid, $C_{17}H_{18}O_4$ (formula 51), MW=286.33

This substance is prepared from 12.4 g (0.046 mole) of (cyclohexyl-2-oxo-4-4H-[1]-benzopyran-8-yl]acetonitrile. After dilution with water, extraction with chloroform, washing with water and evaporation under vacuum, it is dissolved in a 5% aqueous solution of sodium bicarbonate, the insoluble matter filtered out, cooled, acidified, filtered and recristallized in toluene. Weight obtained: 3.4 g (yield: 25%). $MP_G=180°-182°$ C. IR: $\nu c=O$ (pyrone)=1645 cm$^{-1}$, $\nu c=O$ (acid)=1700 cm$^{-1}$. NMR (DMSO), 11H from 1.0 to 3.0 (multiplet), 2H at 3.87 (singlet), 1H at 6.2 (singlet), 1H at 7.4 (triplet, J=8 Hz), 1H at 7.72 (double duplet, J₁=8 Hz, J₂+2 Hz), 1H at 7.97 (double duplet, J₁=8 Hz, J₂=2 Hz).

| Weight analysis: | C % | H % | O % |
|---|---|---|---|
| Calculated: | 71.31 | 6.34 | 22.35 |
| Determined: | 71.48 | 6.35 | |

EXAMPLE 51

(Oxo-4-phenyl-3-4H-[1]-benzopyran-8-yl)acetic acid, $C_{17}H_{12}O_4$, (formula 52), MW=280.28

A mixture of 4.8 g (0.1 mole) of a 50% suspension of sodium hydride in oil and 120 ml of anhydrous dioxane has added to it drop by drop a solution of 33.1 g (0.1 mole) of tetraethyl dimethylaminomethylene diphosphonate (C. R. Degenhardt, Synth. Commun. 1982, 12, 415) in 120 ml of dioxane. This is stirred for one hour at 25° C., and then a solution of 25 g (0.1 mole) of oxo-4-phenyl-3-4H-[1]-benzopyrancarboxaldehyde-8 in 120 ml of dioxane is added drop by drop. This is heated to 50° C. for one hour, then evaporated under vacuum, taken up in water, extracted in chloroform and evaporated under vacuum. The residue is taken up with 1.5 l of concentrated hydrochloric acid and heated with reflux for 30 min. It is cooled, diluted with iced water, extracted with chloroform, washed with water, dried and evaporated under vacuum. The residue is taken up with 300 ml of a 5% aqueous solution of sodium bicarbonate using a reflux, filtered, the filtrate is cooled and acidified (6N HCl). The pasty precipitate obtained is extracted with chloroform, dried and evaporated under vacuum. The residue is purified by chromatography ($SiO_2$, $C_6H_6$-AcOH-MeOH-45:8:8), then recristallized in toluene. Weight obtained: 1.1 g. $MP_G$=137°–139° C.

IR: $\nu c$=0 (pyrone)=1640 cm⁻¹; $\nu c$=0 (acid)=1730 cm⁻¹. NMR (CDCl₃), 2H at 3.97 (singlet), 7H from 7.1 to 7.8 (multiplet), 1H at 8.05 (singlet), 1H at 8.3 (double duplet, J₁=8 Hz, J₂=2 Hz), 1H at 8.8 (exchangable with D₂O).

| Weight analysis: | C % | H % | O % |
|---|---|---|---|
| Calculated: | 72.85 | 4.32 | 22.83 |
| Determined: | 72.83 | 4.50 | |

EXAMPLE 52

[Oxo-4-(phenylmethyl)-2-4H-[1]-benzopyran-8-yl]acetic acid, $C_{18}H_{14}O_4$, (formula 53), MW=294.31

This substance is prepared as in example 2 from 7 g (0.25 mole) of [oxo-4-(phenylmethyl)-2-4H-[1]-benzopyran-8-yl]acetonitrile. Weight obtained: 2.7 g (yield: 36%). $MP_G$=143°–145° C. (toluene). IR: $\nu c$=0 (pyrone)=1640 cm⁻¹; $\nu c$=0 (acid)=1720 cm⁻¹. NMR (CDCl₃), 2H at 3.87 (singlet), 2H at 3.93 (single), 1H at 6.27 (singlet), 9H from 7.0 to 8.3 (multiplet).

| Weight analysis: | C % | H % | O % |
|---|---|---|---|
| Calculated: | 73.46 | 4.79 | 21.75 |
| Determined: | 73.40 | 4.82 | |

EXAMPLE 53

(Diphenyl-2,3-oxo-4-4H-[1]-benzopyran-8-yl)acetonitrile, $C_{23}H_{15}NO_2$, (formula 54), MW=337.38

This substance is prepared as in example 1 from 22.5 g (0.057 mole) of bromomethyl-8-diphenyl-2,3,-4H-[1]-benzopyranone-4 and 7.6 g of potassium cyanide. Weight obtained: 7.1 g (yield: 36%). $MP_K$=185° C. IR: $\nu c$=0 (pyrone)=1630 cm⁻¹. NMR (CDCl₃), 2H at 4.0 (singlet), 12H from 7.0 to 8.0 (multiplet), 1H at 8.3 (double duplet, J₁=8 Hz, J₂=2 Hz).

EXAMPLE 54

(Diphenyl-2,3-oxo-4-4H-[1]-benzopyran-8-yl) acetic acid, $C_{23}H_{16}O_4$, (formula 55), MW=356.38

This substance is prepared as in example 2 from 7.1 g (0.021 mole) of (diphenyl-2,3-oxo-4-4H-[1H]-benzopyran-8-yl)acetonitrile. Weight obtained: 2.4 g $MP_G$=220°–224° C. IR: $\nu c$=0 (acid)=1730 cm⁻¹, $\nu c$=0 (pyrone)=1630 cm⁻¹, $\nu OH$=2900 to 3600 cm⁻¹. NMR(DMSO), 1H at 3.5 (exchangable with D₂O), 2H at 4.0 (singlet), 13H from 7.0 to 8.3 (multiplet).

| Weight analysis: | C % | H % | O % |
|---|---|---|---|
| Calculated: | 77.51 | 4.53 | 17.96 |
| Determined: | 77.29 | 4.51 | |

EXAMPLE 55

(Methyl-2-oxo-4-4H-[1]-benzopyran-8-yl)acetonitrile, $C_{12}H_9NO_2$, (formula 56), MW=199.21

This substance is prepared as in example 1 from 8.8 g (0.034 mole) of bromo-methyl-8-methyl-2-4H-[1]-benzopyranone-4. Weight obtained: 5.1 g.

IR: $\nu c$=N=2250 cm⁻¹, $\nu c$=0 (pyrone)=1650 cm⁻¹. NMR (CDCl₃), 3H at 2,4 (singlet), 2H at 3.97 (singlet), 1H at 6.2 (singlet) 1H at 7.4 (triplet, J=8 Hz, 1H at 7.7 (double duplet, J₁=8 Hz, J₂=2 Hz), 1H at 8.2 (double duplet, J₁=8 Hz, J₂=2 Hz).

EXAMPLE 56

(Methyl-2-oxo-4-4H-[1]-benzopyran-8-yl)acetic acid, $C_{12}H_{10}O_4$, (formula 57), MW=218.21

This substance is prepared as in example 2 from 5 g (0.025 mole) of (methyl-2-oxo-4-4H-[1]-benzopyran-8-yl)acetonitrile. After treatment with sodium bicarbonate and acidification, the substance is purified by chromotography. ($SiO_2$, $C_6H_6$-$CH_3$-COOH-MeOH, 45:8:8) and then recristallized in a water/acetic acid mixture. Weight obtained: 0.6 g. $MP_G$=230°–233° C. IR: $\nu c$=0 (acid)=0 (acid)−1720 cm⁻¹, $\nu c$=0 (pyrone)=1635 cm⁻¹, $\nu c$=0 (pyrone)=2300 to 3300 cm⁻¹. NMR (DMSO), 3H at 2.36 (singlet), 1H at 3.4 (exchangeable with D₂O), 2H at 3.83 (singlet), 1H at 6.25 (singlet), 1H at 7.4 (triplet, J=8 Hz), 1H at 7.7 (double duplet, J₁=8 Hz, J=2 Hz), 1H at 7.9 (double duplet, J₁=8 Hz, J₂=2 Hz).

We claim:

1. (Oxo-4-4H-(1-benzopyran-8-yl)alkanoic acid, described by the formula

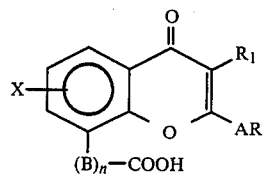

in which AR is a phenyl radical, phenyl substituted by lower alkyl, or lower alkoxy; B is a lower linear or branched alkylene or alkenylene radical; R₁ is hydrogen or a phenyl radical, X is hydrogen or a lower alkyl or alkoxy radical and n=1, or an alkali metal salt thereof.

2. An ester of the compounds according to claim 1, described by the formula

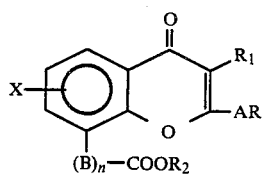

where AR, B, R₁, X and n have the same meanings as before, R₂ is a lower alkyl, a lower hydroxyalkyl, a lower dialkylamino lower alkyl, or morpholinoethyl radical.

3. A compound according to claim 2 wherein R₂ is lower alkyl or hydroxy lower alkyl.

4. An amido of the compounds described in claim 1 described by the formula

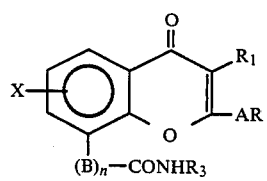

where AR, B, R₁, n and X have the same meanings as previously, and R₃ is a dialkylaminoalkyl radical.

5. (Oxo-4-4H-(1)-benzopyran-8-yl)alkanoic acid or an ester thereof, having the formula:

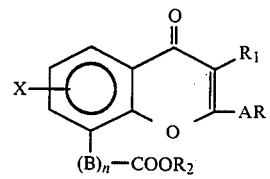

in which AR is phenyl substituted by lower alkyl or lower alkoxy, B is a lower linear or branched alkyenylene or alkylene radical; R₁ is hydrogen or phenyl; X is hydrogen, lower alkyl or lower alkoxy; n=1; R₂ is hydrogen when the compound is an alkanoic acid; R₂ is a lower alkyl, a lower hydroxy alkyl, a lower dialkylamino lower alkyl, or a morpholinoethyl when the compound is an ester; or an alkali metal salt of said acid.

6. An anti-tumor composition containing an anti-tumor effective amount of an acid according to claim 1, having the formula

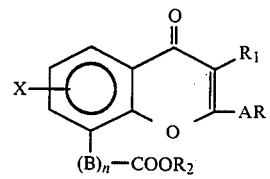

wher AR is a phenyl radical, phenyl substituted by lower alkyl or lower alkoxy, B is a linear or branched lower alkylene radical; R₁ is hydrogen or a phenyl radical, X is hydrogen or a lower alkyl or alkoxy radical and n=1, or alkali metal salts thereof along with a pharmaceutically acceptable carrier.

7. An anti-tumor composition containing an anti-tumor effective amount of a compound according to claim 2, along with a pharmaceutically acceptable carrier.

8. An anti-tumor composition containing an anti-tumor effective amount of an amide according to claim 4 along with a pharmaceutically acceptable carrier.

9. An anti-tumor composition comprising an anti-tumor effective amount of a compound according to claim 5, together with a pharmaceutically acceptable carrier therefor.

* * * * *